(12) United States Patent
Zinaty et al.

(10) Patent No.: US 7,577,283 B2
(45) Date of Patent: Aug. 18, 2009

(54) SYSTEM AND METHOD FOR DETECTING CONTENT IN-VIVO

(75) Inventors: Ofra Zinaty, Haifa (IL); Daniel Buzaglo, Yoqucam (IL); Shlomo Lewkowicz, Kiryat Tivan (IL)

(73) Assignee: Given Imaging Ltd., Yoqneam (IL)

( * ) Notice: Subject to any disclaimer, the term of this patent is extended or adjusted under 35 U.S.C. 154(b) by 164 days.

(21) Appl. No.: 11/358,292

(22) Filed: Feb. 22, 2006

(65) Prior Publication Data

US 2007/0076930 A1  Apr. 5, 2007

Related U.S. Application Data

(63) Continuation-in-part of application No. 11/239,208, filed on Sep. 30, 2005.

(51) Int. Cl.
*G06K 9/00* (2006.01)
(52) U.S. Cl. .................. 382/128; 348/45; 348/65; 348/72; 600/101; 396/17
(58) Field of Classification Search .................. 382/128
See application file for complete search history.

(56) References Cited

U.S. PATENT DOCUMENTS

| | | | |
|---|---|---|---|
| 3,971,362 A | 7/1976 | Pope et al. |
| 4,278,077 A | 7/1981 | Mizumoto |
| 4,689,621 A | 8/1987 | Kleinberg |
| 4,844,076 A | 7/1989 | Lesho et al. |
| 4,920,045 A | 4/1990 | Okuda et al. |
| 5,279,607 A | 1/1994 | Schentag et al. |
| 5,447,868 A | 9/1995 | Augurt |
| 5,563,071 A | 10/1996 | Augurt |
| 5,604,531 A | 2/1997 | Iddan et al. |
| 5,819,736 A | 10/1998 | Avny et al. |
| 5,993,378 A | 11/1999 | Lemelson |
| 6,166,496 A | 12/2000 | Lys et al. |
| 6,228,605 B1 | 5/2001 | Marshall |
| 6,240,312 B1 | 5/2001 | Alfano et al. |
| 6,310,642 B1 | 10/2001 | Adair et al. |

(Continued)

FOREIGN PATENT DOCUMENTS

DE        29 29 429        2/1980

(Continued)

OTHER PUBLICATIONS

Tjoa, M.P, Krishnan, S.M., "Feature extraction for the analysis of colon status from the endoscopic images", Biomed Eng Online. 2003;2: 9, April 8, 2003, doi: 10.1186/1475-925X-2-9.*

(Continued)

*Primary Examiner*—Matthew C Bella
*Assistant Examiner*—Sath V. Perungavoor
(74) *Attorney, Agent, or Firm*—Pearl Cohen Zedek Latzer, LLP

(57) ABSTRACT

A system and method for detecting in-vivo content, may include an in-vivo imaging device for capturing a stream of image frames in a GI tract, a content detector for detecting and/or identifying one or more image frames from the stream of image streams that may show content, and a graphical user interface (GUI) to display image frames detected.

12 Claims, 5 Drawing Sheets

U.S. PATENT DOCUMENTS

| | | | |
|---|---|---|---|
| 6,402,686 | B1 | 6/2002 | Ouchi |
| 6,402,687 | B1 | 6/2002 | Ouchi |
| 6,459,919 | B1 | 10/2002 | Lys et al. |
| 6,584,348 | B2 | 6/2003 | Glukhovsky |
| 6,632,175 | B1 | 10/2003 | Marshall |
| 6,904,308 | B2 | 6/2005 | Frisch et al. |
| 7,215,338 | B2 | 5/2007 | Horn et al. |
| 2001/0034025 | A1 | 10/2001 | Modlin et al. |
| 2001/0035902 | A1 | 11/2001 | Iddan et al. |
| 2002/0103417 | A1 | 8/2002 | Gazdzinski |
| 2002/0173718 | A1 | 11/2002 | Frisch et al. |
| 2003/0002624 | A1 | 1/2003 | Rinaldi et al. |
| 2003/0190064 | A1* | 10/2003 | Inoue .................. 382/128 |
| 2005/0075537 | A1* | 4/2005 | Chen et al. .............. 600/109 |
| 2006/0036166 | A1 | 2/2006 | Horn |

FOREIGN PATENT DOCUMENTS

| | | |
|---|---|---|
| DE | 34 40 177 | 5/1986 |
| EP | 1159917 | 5/2001 |
| FR | 2688997 | 10/1993 |
| IL | 126727 | 10/1998 |
| IL | 143259 | 8/2006 |
| JP | 5745833 | 3/1982 |
| JP | 4109927 | 4/1992 |
| JP | 4144533 | 5/1992 |
| JP | 5015515 | 1/1993 |
| JP | 19946-114037 | 4/1994 |
| JP | 6142081 | 5/1994 |
| JP | 6285044 | 10/1994 |
| JP | 07111985 | 5/1995 |
| JP | 7289504 | 11/1995 |
| JP | 2000342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001231744 | 8/2001 |
| JP | 2001245844 | 9/2001 |
| JP | 2002010990 | 12/2001 |
| JP | 2000342524 | 6/2002 |
| JP | 2000342525 | 6/2002 |
| WO | WO 99/32028 A2 | 7/1999 |
| WO | WO 01/10291 A1 | 2/2001 |
| WO | WO 01/50941 | 7/2001 |
| WO | WO 01/69212 A1 | 9/2001 |
| WO | WO 02/055984 A2 | 7/2002 |
| WO | WO 02/067593 A1 | 8/2002 |
| WO | WO 02/094337 A2 | 11/2002 |
| WO | WO 03/003706 | 1/2003 |
| WO | WO 03/011103 A2 | 2/2003 |
| WO | WO 04/028336 A2 | 4/2004 |
| WO | WO 04/035106 A2 | 4/2004 |

OTHER PUBLICATIONS

Kang, J., Doraiswami, R., "Real-time image processing system for endoscopic applications", Electrical and Computer Engineering, 2003. IEEE CCECE 2003. Canadian Conference on, May 4-7, 2003, vol. 3, On pp. 1469-1472 vol. 3, ISBN: 0-7803-7781-8.☐☐.*

Chindaro, S., Sirlantzis, K., Deravi, F., "Colour space fusion for texture recognition", Video/Image Processing and Multimedia Communications, 2003. 4th EURASIP Conference focused on Jul. 2-5, 2003, vol. 1, On pp. 181-186 vol. 1, ISBN: 953-184-054-7.*

U.S. Appl. No. 09/800,470, filed Mar. 8, 2001, Iddan et al.

The Radio Pill, Rowlands, et al., British Communications and Electronics, Aug. 1960. pp. 598-601.

Video Camera to "TAKE"—RF System lab, Dec. 25, 2001.

Wellesley company sends body monitors into space—Crum, 1998.

Wireless transmission of a color television moving image from the stomach using a miniature CCD camera, light source and microwave transmitter. Swain CP, Gong F. Mills TN. Gastrointest Endosc 1997;45:AB40.

BBC News Online—Pill camera to 'broadcast from the gut', Feb. 21, 2000, www.news.bbc.co.uk.

Machine Vision: Theory, Algorithms, Practicalities—E.R. Davies, 1990.

Non-Lambertian Shading and Photometric Stereo—Tagare, et al., SPIE vol. 1260 Sensing and Reconstruction of Three-Dimensional Objects and Scenes (1990).

Robust shape reconstruction from combined shading and stereo information—Lee, et al., SPIE vol. 1771 Applications of Digital Image Processing XV (1992), pp. 171-182.

Shedding light on cancer diagnosis—Powell (Ed.), May 2000, Laser Focus World.

Simulation of images by photometric stereo modeling, Russell, et al., Optical Engineering, Sep. 1991, vol. 30, No. 9, pp. 1337-1345.

Two Image Photometric Stereo Method, Yang et al. SPIE vol. 1826, Intelligent Robots and Computer Vision XI (1992).

www.oceanoptics.com—pH Sensor & Accessories, ©2001.

Mackay, R. Stuart, Bio-medical Telemetry: Sensing and Transmitting Biological Information from Animals and Man, 1970, pp. 244-245, Second Edition, John Wiley & Sons, Inc., pp. 244-45 (1970).

Yarbrough, III M.D., Dabney R. et al., "Evaluation of the Heidelberg pH Capsule: Method of Tube less Gastric Analysis", The American Journal of Surgery, vol. 117, pp. 185-192, Feb. 1969.

Lange, H. et al., The "Heidelberg Capsule"- A Micro-Transmitter for measuring stomach pH, pp. 1-10. 2008.

Craford, George et al., "In Pursuit of the Ultimate Lamp", Scientific American, Feb. 2001, pp. 49-53.

Wang, Lei et al., "Integrated Micro-Instrumentation for Dynamic Monitoring of the Gastro-Intestinal Tract", Department of Electronics and Electrical Engineering, University of Glasgow, pp. 1-4, May 2002.

International Search Report for International Application No. PCT/IL02/00391, May 19, 2003.

International Search Report for International Application No. PCT/IL99/00554, Apr. 4, 2000.

Katzgraber, F. et al., "Mechanism of fatal air embolism after Gastrointestinal Endoscopy", International Journal of Legal Medicine, vol. III, No. 3, Apr. 1998, abstract.

Manual of Photogrammetry, Morris M. Thompson, ed., Chapter XVI, Transformation and Rectification, vol. II, No. 3, American Society of Phtogrammetry, Virginia, pp. 812-813 (1966).

"New Smart Plastic has good rnemory"-Turke, European Medical Device Manufacturer, devicelink.com. 2008.

Shin-Ichi Torikai et al., "Robots for the Future", http://jin.jcic.or.jp/nipponia/nipponia13/sp05.html., printed Nov. 29, 2001.

Supplementary Partial European Search Report for European Patent Application EP 99 95 1074, Mar. 9, 2004.

"The Heidelberg pH Capsule System Telemetric Fasting Gastric Analysis", product specification. 2008.

Chan, Jason, "Tiny Cam", http://www.jason.net/tinycam.htm., printed Dec. 18, 2001.

"Review proves the value of computers", http://middleeasthealthmag.com/article2.htm., printed Nov. 29, 2001.

Personal Electronic Devices, Inc., http://www.pedinc.com, 1997, Apr. 13, 1998.

"The Norika V3 Capsule Camera has landed! the Robotic Capsule for Diagnosis and Treatment Inside a Patient", http://www.rfnorika.com, printed Jan. 1, 2002.

Davies, et al., "Detection of the Cancer-Prone Colon, Using Transepithelial Impedence Analysis", Arch Surg-vol. 124, Apr. 1989, pp. 480-484.

* cited by examiner

SYSTEM AND METHOD FOR DETECTING CONTENT IN-VIVO

CROSS REFERENCE TO RELATED APPLICATION

This application is a continuation in part of patent application Ser. No. 11/239,208, filed Sep. 30, 2005, entitled "System and Method for Detecting Content In-Vivo", which is incorporated by reference herein in its entirety.

FIELD OF THE INVENTION

The present invention relates to a method and system for detection of content in-vivo, and specifically within the gastrointestinal (GI) tract.

BACKGROUND OF THE INVENTION

Devices helpful in providing in-vivo imaging are known in the field. Autonomous in-vivo imaging devices, such as swallowable or ingestible capsules or other devices may move through a body lumen, imaging as they move along.

An in-vivo device may collect data from different points along a body lumen, for example lumens of the GI tract, and transmit the data externally for analysis and diagnosis. The GI tract is a very long and curvy path which usually includes content. Content within the body lumens may be any fluid, solid, liquid, gas, particle, feces, rough reduces, fluid bile, or any substance that is not a permanent or stagnant substance within the body lumen.

SUMMARY OF THE INVENTION

According to some embodiments of the present invention, an in-vivo imaging system may include an algorithm for identifying and detecting content. According to some embodiments of the present invention the algorithm may identify whether a structure or a number of pixels may be identified as possibly showing content.

According to some embodiments of the present invention, a visual presentation of the content information e.g. a percentage of content in the image of pixels or the cleansing level of the image of pixels, may be in the form of a color bar, for example where different colors may represent different quantities of content. In other embodiments, the visual representation may be a graph, for example a line graph or a bar graph. In other examples, the percentage of content in the image stream or the cleansing index may be presented and/or displayed in numerical format. Other types and more than one type of visual presentations may be implemented.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
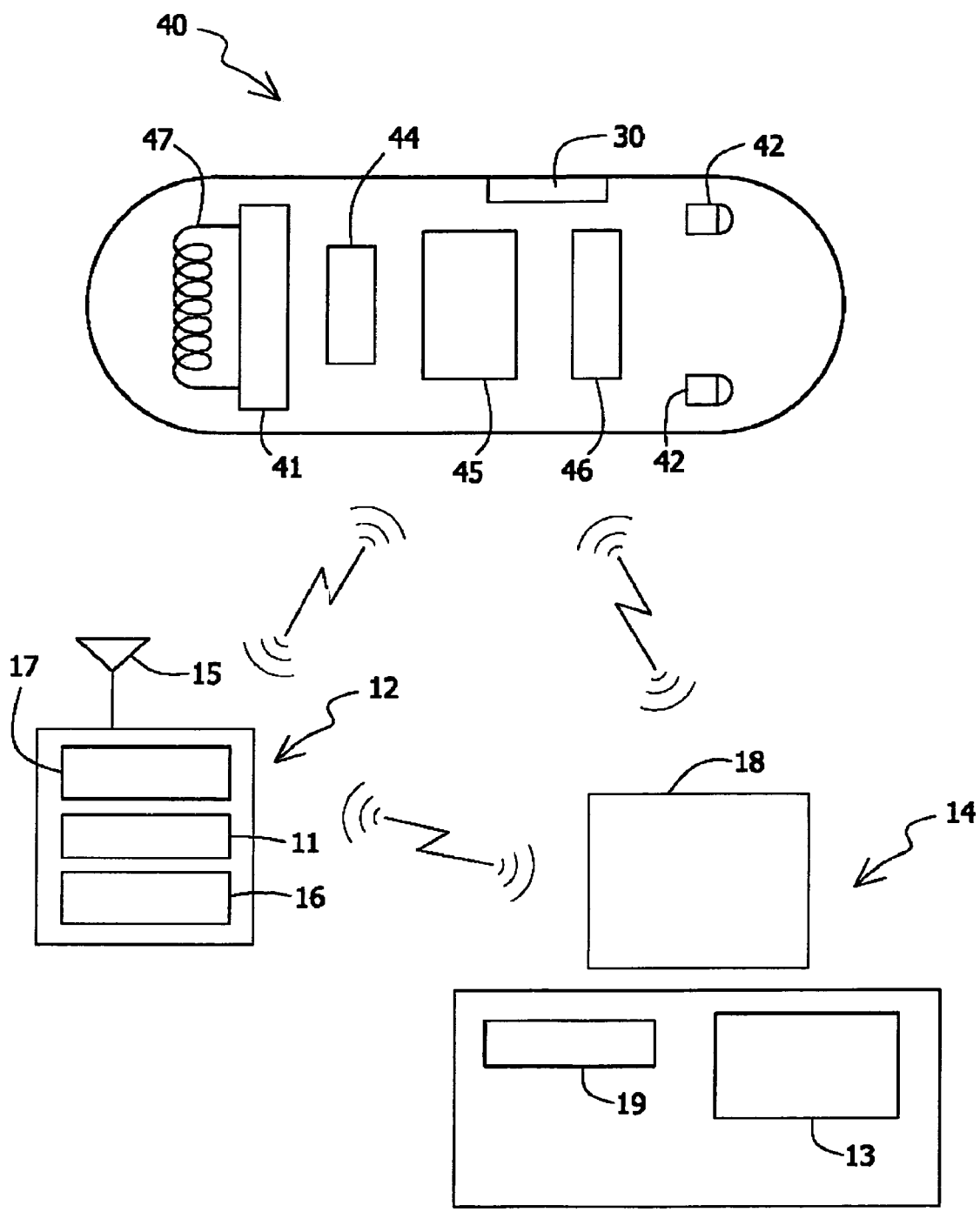
FIG. 1 is a schematic illustration of an in-vivo imaging system according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the following detailed description, numerous specific details are set forth in order to provide a thorough understanding of the present invention. However, it will be understood by those skilled in the art that the present invention may be practiced without these specific details. In other instances, well-known methods, procedures, and components have not been described in detail so as not to obscure the present invention.

Embodiments of the present invention, describe a system, and method for detecting content, for example by providing a system, and method for automatically, without a user intervention, identifying, detecting, selecting, and marking image frames captured in the GI tract that may indicate the presence of content. The selected image frames may be displayed to a health professional for diagnosis. According to one embodiment of the present invention, an autonomous in-vivo imaging device, for example an imaging device in the form of a swallowable capsule, may capture a series of image frames of a body lumen as well as other information from within or along a body lumen and may transmit the captured images and other information to one or more external units. Analysis of the transmitted data may be used to automatically and/or machine select and mark image frames that may be candidates for content identification. Analysis and processing of the data may be performed automatically without user intervention. Machine selection, detection and/or marking of image frames that may be candidates for content identification may be performed at least partially by a content detector and such that user intervention in the detection of image frames that may be candidates for content identification may not be required. Machine selection, detection and/or marking may be performed by, for example, one or more processors, a workstation, circuitry, a sensor or any other computation and/or sensing able device. According to some embodiments of the present invention, selected images may be displayed to a health professional for diagnosis. In some embodiments of the present invention, screening may also be facilitated with data that may be partially occluded by content. For example, image frames may be captured in an environment that may be partially occluded with content, for example content that may be present within a body lumen, e.g. colon.

Reference is made to FIG. 1, which shows a schematic diagram of an in-vivo imaging system according to an embodiment of the present invention. Typically, the in-vivo imaging system may include an in-vivo imaging device 40, an external receiving device and/or recording device 12, e.g. data receiver, and a workstation 14. The in-vivo imaging device 40 may have an imager 46, for capturing image frames or a stream of image frames, an illumination source 42, for illuminating the body lumen, a power source 45 for powering device 40, a processor 44 for processing data and commands to and from device 40, and a transmitter 41 with antenna 47, for transmitting image and possibly other data to an external receiver 12. In some embodiments of the present invention, in-vivo device 40 may include one or more sensors 30, in addition to imager 46, for example, temperature sensors, pH sensors, pressure sensors, blood sensors, tracking sensors, etc. Imager 46 may be a CCD or CMOS imager, or may be another solid state imaging device or other imaging device. Illumination source 42 may include one or more LEDs or other illumination sources. In some embodiments of the present invention, device 40 may be an autonomous device, a capsule, or a swallowable capsule. In other embodiments of the present invention, device 40 may not be autonomous, for example, device 40 may be an endoscope or other in-vivo imaging device.

The in-vivo imaging device 40 may typically, according an embodiment of the present invention, transmit information (e.g., images or other data) to an external receiver 12 possibly close to or worn on a subject. Typically, the receiver 12 may include an antenna or antenna array 15 and a data receiver storage unit 16. Typically antenna array 15 may pick up signals transmitted by device 40 or the transmitter 41 and antenna 47 of device 40. The external receiver 12 may include one or more processors 17 for processing image data or other data. Receiver 12 may include a tracking unit 11, for tracking the location of an autonomous in-vivo imaging device 40 over time. For example, tracking unit 11 may track the location of device 40 in three dimensional space over time and/or may track the distance, for example the distance over time that device 40 traveled through the GI tract or through a specific organ in the GI tract over time. Tracking unit 11 may be similar to various embodiments described, for example, in US Patent Application Publication No. US-2002-0173718-A1 published on Nov. 21, 2002 and U.S. patent application Ser. No. 10/879,053 filed on Jun. 30, 2004 both of which are assigned to the common assignee of the present application and incorporated herein by reference in their entirety. Other known tracking units or methods of tracking a device may be used. In other embodiments, the tracking unit 11 or part of its functionality may be included in device 40. The receiver 12 may take on other suitable configurations and may not include an antenna or antenna array. In one embodiment of the present invention, the receiver 12 may, for example, include a LCD display for displaying image data or other data, e.g. tracking data. In other embodiments, receiver 12 may be electrically connected, e.g. via wire, blue tooth, or wireless connection, to a display unit, e.g. display unit 18 or workstation 14, to display data transmitted by in-vivo device 40 and/or processed by processing unit 17, 44, or workstation 14.

In one embodiment of the present invention, receiver 12 may, for example, receive and store data from imaging device 40, e.g. an image stream data captured and/or processed by processor 17 and later transfer the received data to a workstation 14, such as a personal computer, laptop or other portable or stationary computing devices, where the data may be further analyzed, stored, and/or displayed to a user, e.g. a health professional. Typically, workstation 14 may include processing unit 13, data processor storage unit 19, a disk drive, input-output devices, and display unit 18, e.g. a monitor, although alternate configurations are possible. Processing unit 13 may typically, as part of its functionality, act as a controller controlling the display of data for example, image data or other data. In one example, processor 13 and/or processor 17 may be employed to construct a content screening movie from candidate image frames selected by the content detector. Display unit 18 may typically be a conventional video display, but may, in addition, be any other device capable of providing image or other data Instructions or software for carrying out a method according to an embodiment of the invention may be included as part of workstation 14, for example stored in memory 19. According to some embodiments of the present invention, a content detector may be included, for example as part of the functionality of processor 13, processor 44 and/or processor 17 and may select from an image stream, one or more image frames that may be candidates for content identification. In another embodiment, a content detector may be included as part of the functionality of the solid state imaging device, e.g. imager 40. In yet another embodiment, content detector may be included as part of the functionality of an ASIC (application specific integrated circuit), for example and ASIC included in device 40. In one example, the content detector may be a series of commands or an algorithm that may be implemented to detect in one or more image frames, for example a stream of image frames, the presence of predetermined features and/or parameters. Based on the detection, candidate image frames may be selected. Output from the content detector may be transferred to a display unit 18, a display unit included in receiver 12 and/or processing unit 13 or 17 by either wired or wireless communication.

In other embodiments, each of the various components need not be required; for example, the in-vivo device 40 may transmit or otherwise transfer (e.g., by wire) data marking image frames that may be candidates for content identification directly to a viewing device or workstation 14. In one embodiment of the present invention, device 40 may only transmit selected image frames that may be candidates for content identification.

In-vivo imaging systems suitable for use with or adaptation to embodiments of the present invention may be similar to various embodiments described, for example in U.S. Pat. No. 5,604,531, entitled "In-Vivo Video Camera System", assigned to the common assignee of the present application and incorporated herein by reference in its entirety, and/or U.S. patent application Ser. No. 09/800,470, filed Mar. 1, 2000 and/or US Patent Application Publication Number 20010035902 published on Nov. 1, 2001 and entitled "Device and System for In-Vivo Imaging", also assigned to the common assignee of the present application and incorporated herein by reference in its entirety.

Other in-vivo systems, having other configurations, may be used. Of course, devices, systems, structures, functionalities and methods as described herein may have other configurations, sets of components, processes, etc.

In some embodiments of the present invention, an in-vivo device such as imaging device 40 may be swallowed, or otherwise inserted within a gastrointestinal (GI) tract and may pass through the GI tract, for example, via natural peristaltic motion while capturing a series of image frames, e.g. capturing image frames periodically at two frames per second. In other embodiments of the present invention, the in-vivo imaging device may advance through the GI tract via other suitable means and may capture image frames at other suitable rates, for example, at variable rates. Image frames captured as well as other data may be transmitted externally for processing and display. According to one embodiment of the present invention, tracking data, tracking the location of the in-vivo imaging device over time or over the course through the GI tract may be included in the processing and display of data. For example, tracking data may be used to indicate the point, e.g. the image frame, at which content screening should begin, e.g. the tracking system may detect entrance into the colon. Data captured may be processed to automatically select image frames that may be candidates for content diagnosis.

Figure 2:
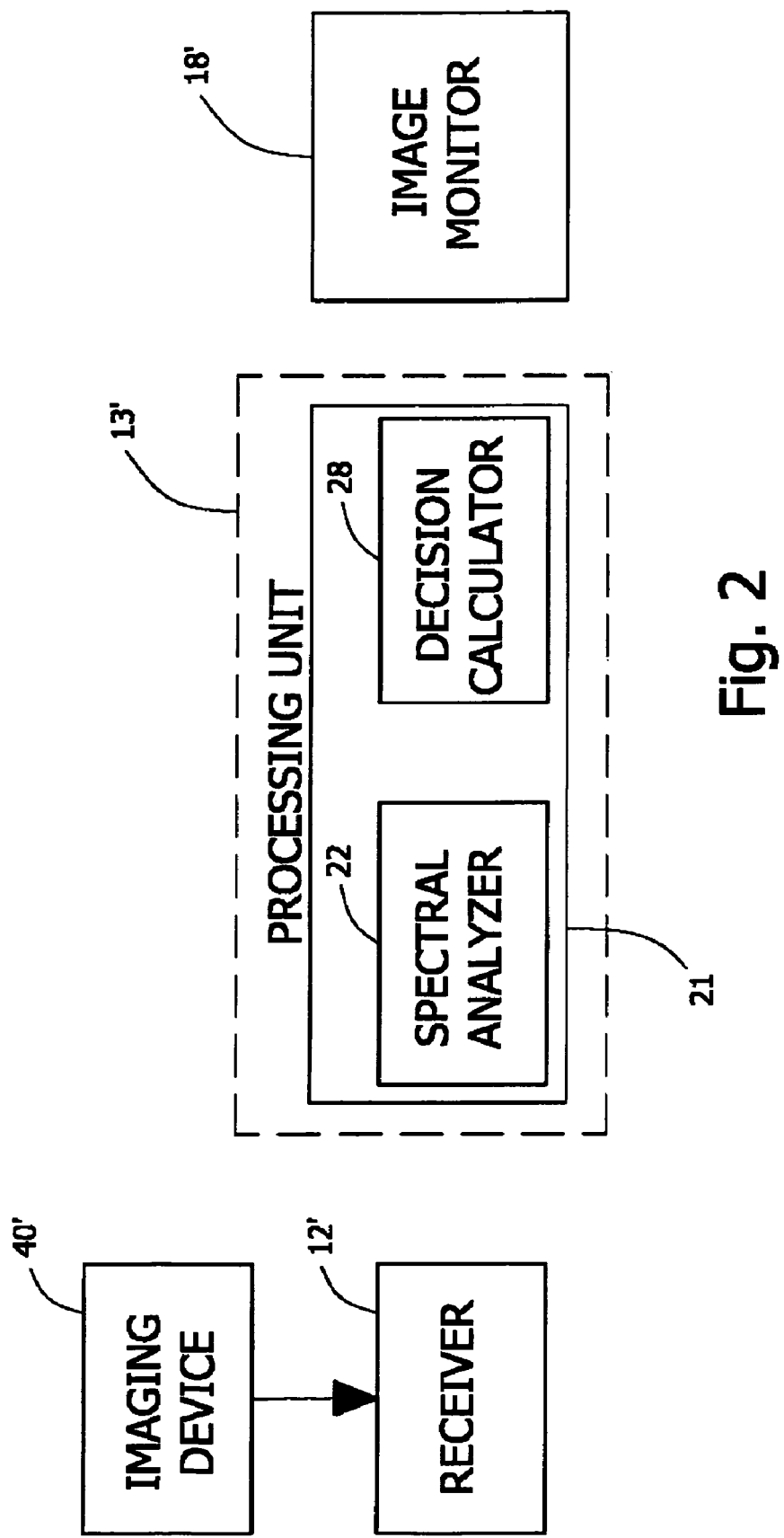
FIG. 2 is a block diagram illustration of a system for detecting content, according to one embodiment of the present invention.
Figure 3:
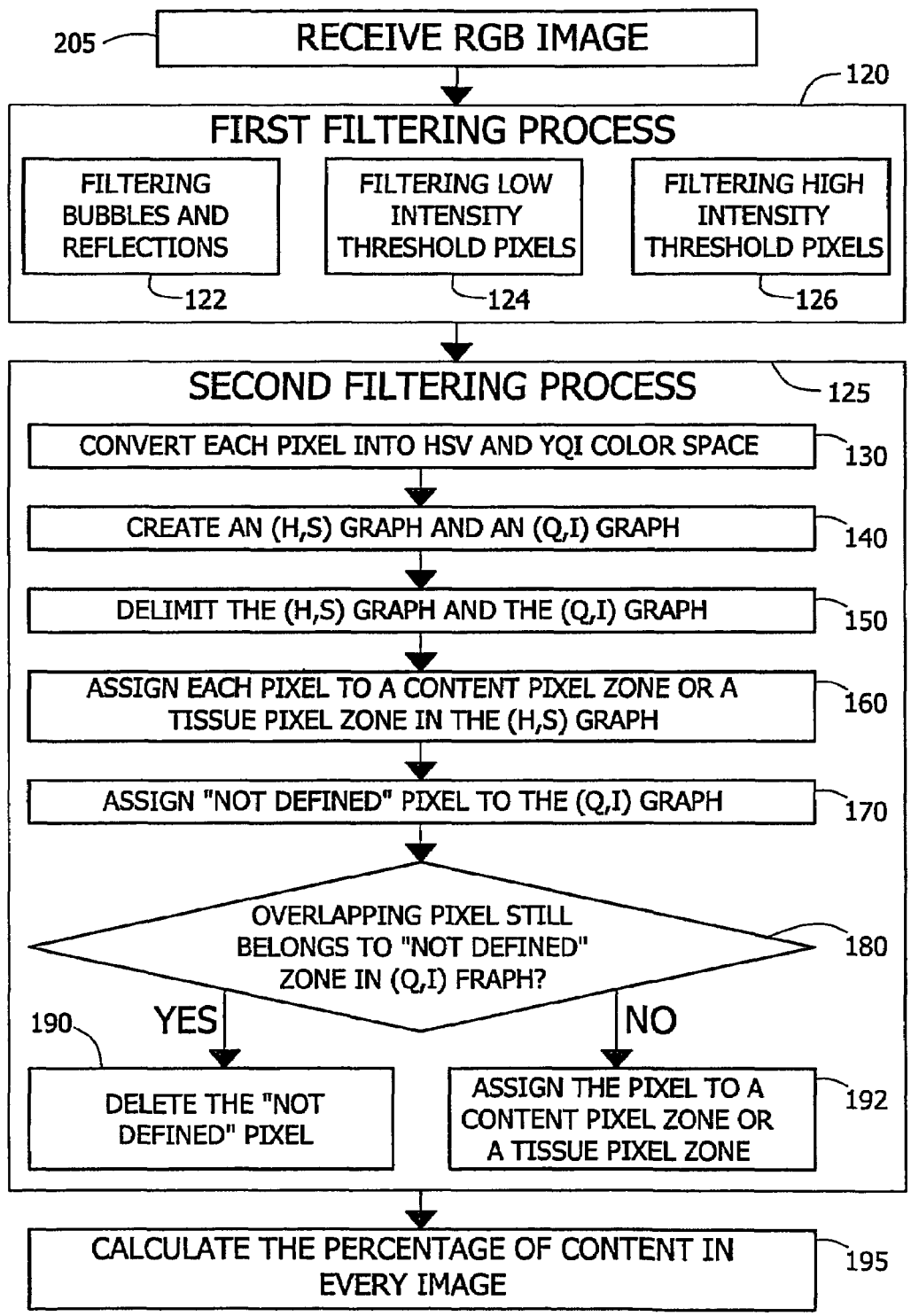
FIG. 3 is a flow chart illustration of a method, according to one embodiment of the present invention.

Reference is now made to FIGS. 2 and 3, which illustrate a system 50 and a flow chart showing an embodiment of a method for detecting content or any other color-distinguishable pathology, for example within the gut. According to some embodiments of the present invention, system 50 may include an imaging device 40', a receiver 12', a processing unit 13', and an image monitor 18'. System 50 may be similar to the system shown in FIG. 1. In one example, processing unit 13' may be employed to construct a content screening movie from candidate image frames selected by the content detector. Processing unit 13' may include a content detector 21 which may further include for example an analyzer, such as a spectral analyzer 22, and a decision calculator 28. According to one embodiment of the invention, processing unit 13' may include a standard computer accelerator board, high performance computer, multiprocessor or any other serial or parallel high performance processing machine possibly operating software. Image monitor 18' may be a video display, a graph, a table or any other indicator.

The steps of FIG. 3 may be accomplished using for example system 50 of FIG. 2, the system of FIG. 1 or another suitable system. In one embodiment, images are captured and processed within the device 40'. In another embodiment, images are captured by an in-vivo system, and are transmitted to a remote location where they are processed. In step 110 receiver 12' receives an image of a stream of images, such as an RGB image, captured by the device 40', other types of images may be used. In step 120 processing unit 13' performs a first filtering process, for example on the RGB image 101, which may include, for example filtering bubbles and reflections 122, which may appear in the RGB image. In addition, the first filtering process may include filtering low intensity threshold pixels 124, e.g. luminance pixels and high intensity threshold pixels, and filtering high intensity threshold pixels 126 e.g. maximal band intensity pixels, other features may be filtered. Other features may be filtered. According to some embodiments of the present invention, the filtered pixels may be defined as "don't care pixels", e.g. pixels which will not be considered or calculated, during the content detection process.

Other Filtering may be Used.

According to some embodiments of the present invention, a second filtering process 125, for detecting content, for example in an RGB image, may include one or more processing steps. In step 130, each pixel which was not defined as a "Don't care pixel", in the first filtering process 120 is converted, for example into two different 3D (three dimensions) color spaces e.g. an HSV (Hue Saturation Value) and a YQI (Y-Luminance Q-Quadrature a magenta-green axis, I-Orange-a cyan axis) color spaces.

Other Color Spaces may be Used

Figure 4:
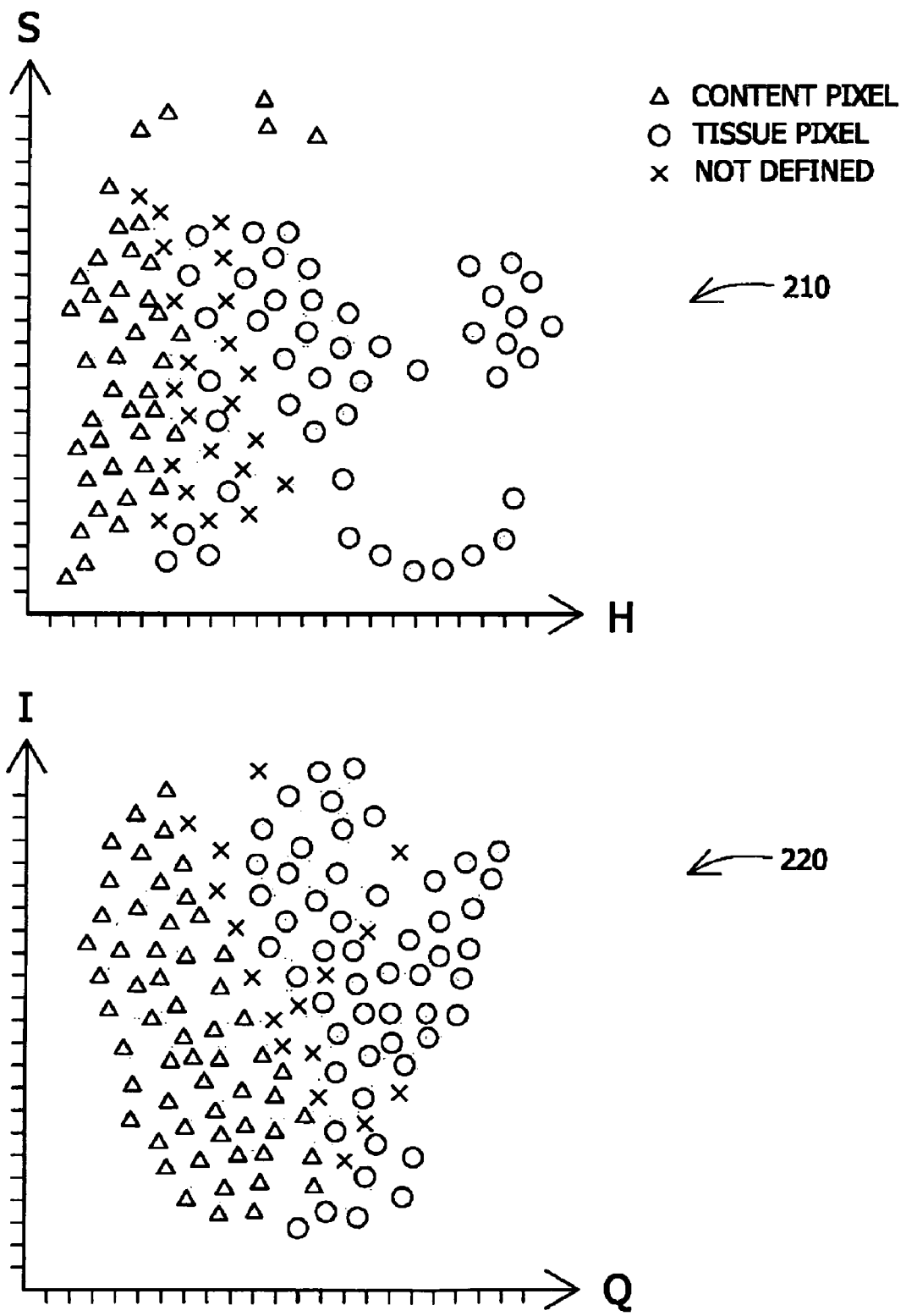
FIG. 4 is a schematic illustrations of two graphs, according to one embodiment of the present invention.

According to some embodiments of the present invention, in step 140 graphs may be constructed according to, for example the HSV and the YQI color spaces. For example, as shown in FIG. 4 an (H, S) color space graph 210 may be created based on the HSV color space and a (Q, I) graph 220 may be created based on the YQI color space. The graphs 210 and 220 may display groups of pixels, for example a group of content pixels (marked 'Δ'), a group of tissue pixels (marked '0') and a group of 'not defined' pixels (which belong to an overlapping zone e.g. a zone which is not a content or a text zone, marked 'x'). In step 150 the (H,S) graph and the (Q,I) graph may be delimited into two hyper planes zones, for example a tissue decision zone and a content decision zone.

In step 160 each pixel of image 101 is assigned to its clustering set in the (H, S) graph e.g. to a content pixel zone or a tissue pixel zone. In step 170 a 'not defined' pixel is assigned to its clustering set in the (Q,I) color space graph. If the 'not defined' pixel still belongs to a 'not defined' pixel zone in the (Q,I) graph it will be deleted in step 190 e.g. defined as a don't care pixel. If the 'not defined' pixel in step 180 doesn't belong to a 'not defined' pixel zone, it will be assigned in step 192 to a content pixel zone or a tissue pixel zone in the (Q,I) graph. In step 195, the percentage of content for each image of the stream of images is calculated using for example the following equation:

$$\frac{\text{percentage of content for each image of the stream of images}}{} = \frac{\text{number of content pixels}}{(\text{number of tissue pixels} + \text{number of content pixels})}$$

According to some embodiments of the present invention display 18 may include a summarized graphical presentation of an in-vivo data stream, for example, a color bar. Typically, the graphical presentation may be a fixed presentation displayed alongside a streaming display of a data stream, for example, an image stream in accordance with some embodiments of the present invention. The graphical presentation may include a series of colors, a series of colored areas, or a series of patterns, image items, images or pixel groups (e.g., a series of stripes or areas of color arranged to form a larger bar or rectangular area), where each, for example, color in the series may be associated with and/or correspond to an element or a group of elements in the original data stream, such as in each image. For example, each colored stripe may correspond to the percentage of content or cleanliness level in each image or group of images from a data stream. Image units other than stripes (e.g., pixels, blocks, etc.) may be used, and the image units may vary in a dimension other than color (e.g., pattern, size, width, brightness, animation, etc). In one embodiment of the invention, the presentation may map out a varying quantity (e.g. a captured data stream) and may, for example, give indication of the relationship between the data stream captured and the anatomical origin or position relative to a start of the captured data stream, for example, the approximate or exact site, for example, in the GI tract from where various data captured may have originated. In another embodiment of the invention, the mapping may give, for example, an indication of an event (e.g. a physiological event) captured, measured, or otherwise obtained. In yet another embodiment of the invention, the mapping may give for example an indication of change of one or more parameters measured over time, for example, a change occurring due to pathology, a natural change in the local environment, or due to other relevant changes.

In some embodiments of the present invention, content may be identified, for example, by image analysis, image processing, color analysis, morphological analysis, shape analysis, by one or more sensor output, by other methods, or by more than one method and/or a combination of methods.

According to one embodiment of the present invention a cleanliness index for the entire image stream or for a subset of the image stream, e.g. a subset of the image stream with images from the colon, may be calculated. For example, a cleanliness index may be defined as:

$$CI_1 = 1 - (\text{number of images frames containing content})/(\text{total number of image frames});$$

wherein the number of images frames containing content and the total number of image frames may be taken from a subset of an original image stream and/or from an entire image stream.

In another embodiment of the present invention a cleanliness index for the entire image stream or for a subset of the image stream, e.g. a subset of the image stream with images from the colon, may be alternately defined. For example, a cleanliness index may be defined as:

$$CI_2 = 1 - \text{AVG}(\text{percent content of each image of the stream});$$

wherein AVG is a function that calculates the average of a plurality of values and wherein percent content of each image of the stream may be defined as may be described herein, e.g. as may be described in FIG. 3. Other suitable methods of defining the cleanliness index may be implemented.

In another example the content index may exclude redundant information in the image frames, e.g. an area in the colon that may be imaged by a number of image frames. In one example, redundancy in image information may be identified by known image processing methods, e.g. registration of images. In other examples, redundancy may be avoided by taking into account an output from a position detection sensor. A position sensor may indicate movement or advancement of the imaging device between capturing of image frames. When the imaging device may linger in an area over a number of frames, the information in some of those frames may be redundant and the redundant information may not be considered when calculating the content index. Other method and more than one method may be used to detect and exclude redundant information within the image frames.

In other embodiments an index other than a content index may be determined and/or calculated. For example, a pathology index, e.g. blood index, a polyp index, or other suitable indices that may be calculated in a similar manner as may be described herein. In one example, an indication of a specified pathology (e.g. bleeding, polyp formation, etc.) in one or more image frame may be identified. The pathology index may be an indicator of a probability that a specific pathology may be present in a body lumen based on the indications and/or features identified in the image frames identified.

Detection may be Based on Color, Shape, Texture, Pattern etc.

Figure 5:
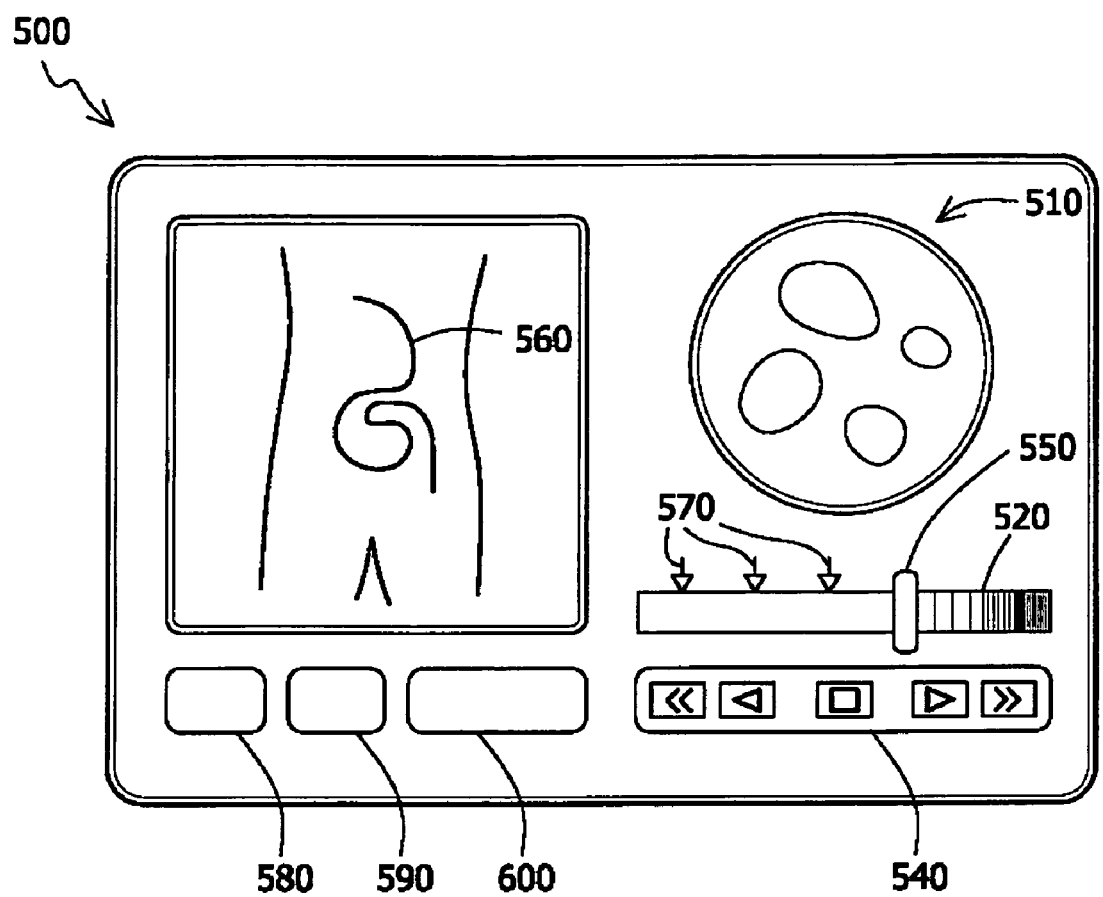
FIG. 5 is a schematic graphical user interface (GUI) according to an embodiment of the present invention.

Reference is now made to FIG. 5 showing schematic screen of a graphical user interface (GUI) that may be used, according to one embodiment, to display a content screening movie including candidate image frames selected for content identification. The content screening movie may include image frames automatically selected by a content detector. According to some embodiments of the present invention, content screening movie window 510 may display a streaming display of image frames while an indicator 550 may advance to a position along a summarized graphical presentation bar 520, a e.g. time/location bar that may indicate from where along the image stream the current frame displayed in movie window 510 may have been obtained. One or more image frames in movie window 510 may, for example, be marked to highlight areas in each frame that may potentially be content as may be described herein. A tracking curve 560 that may track the course of the imaging device may be shown. An indicator similar to indicator 550 may be used on the tracking curve to show correspondence with image frames displayed in window movie 510 and graphical presentation bar 520.

Summarized graphical presentation bar 520 may be similar to summarized graphical presentation bar described for example in US Patent Application Publication Number 20050075551, published on Apr. 7, 2005 which is assigned to the common assignee of the present application and incorporated herein by reference in its entirety or may be similar to other suitable graphical presentations. The position of indicator 550 along bar 520 may be controlled by user input to initiate image streaming in movie window 510 from a specified image frame in the image stream. Markers 570 may indicate from where along bar 520 candidate image frames may have been obtained. Control buttons 540 may be included in the GUI 500 and may allow a user to, for example, fast-forward, rewind, stop, play or reach the beginning or end of an image stream displayed in movie window 510. In one embodiment of the present invention, control buttons 540 may allow a user to choose to view image frames not selected as candidate image frames, for example, to view image frames that may appear in the original image frame directly before or after a candidate image frame. According to some embodiment of the present invention, content screening button 580 may allow a user to initiate a content screening procedure or to initiate streaming of the shortened content movie in movie window 410. In other examples, the automatic content screening may be initiated automatically or at a different point in the overall diagnostic procedure, e.g. during recording, downloading, and/or uploading of image data. In other embodiments of the present invention, one or more image frames may be shown concurrently in movie window 510.

According to one embodiment of the present invention, the cleanliness index may be displayed as for example a numerical presentation, for example in window 600. The cleanliness index may be a cleanliness index of the entire image stream displayed, a pre-defined subset of the image stream, e.g. a subset of the image stream identified as the colon, or may be a user defined subset of the image stream. For example, a user may highlight a section of bar 520 and/or mark a beginning and end point on bar 520 and the numerical representation of the cleanliness index may represent that subset of the image stream selected by the user. Other methods of selecting a subset of an image stream may be implemented. Other methods of displaying the cleanliness index of the image stream may be implemented. In one example, the cleanliness index may help a health professional determine the cleanliness level of the image stream and/or the success of a preparatory procedure for cleaning the GI tract, e.g. the colon in preparation of imaging. The cleanliness index may indicate and/or detect the presence of content within a body lumen.

A user or health professional may select one or more image frames from the movie window 510 to include in a report, e.g. diagnosis report. Markers 570 may be highlighted to indicate that a specific frame has been selected. Additional markers 570, marking non-candidate images may be added by the user. Clicking or otherwise indicating 'make report' button 590 may advance a user to a new screen that may show image frames that the user selected and provide a template for a user to prepare a diagnosis report.

According to some embodiments, the method for detecting content such as the algorithm for identifying and detecting contents as was described in FIG. 3, may be used to detect other color-distinguishable pathology in a body lumen such as varices, veins, blood vessels etc. Other operations or series of operations may be used The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method for determining the presence of content in-vivo, the method comprising:
    capturing a plurality of image frames of a gastrointestinal tract using an imager;
    identifying, using a processor, content in at least one image frame, said content including any fluid, solid, liquid, gas, particle, feces, rough reduces, fluid bile, or any substance that is not a permanent or stagnant substance within a body lumen;
    calculating, using a processor, a percentage of said content in the at least one image frame which was identified to include said content;
    calculating, using a processor, a cleanliness index for the plurality of image frames based on an average of said percentage of content derived from a subset of the plurality of image frames; and
    based on the cleanliness index, determining, using a processor, success of a preparatory procedure for cleaning the gastrointestinal tract.

2. The method according to claim 1 comprising displaying the cleanliness index in numerical format.

3. The method according to claim 1 comprising selecting a subset of image frames from the plurality of image frames.

4. The method according to claim 3 wherein the selecting is performed by a user.

5. The method according to claim 1, comprising inserting an autonomous imaging device in-vivo.

6. The method according to claim 1, comprising tracking a location at which at least the subset of images is captured.

7. A system for detecting in-vivo content, the system comprising:
    an imaging device to capture a plurality of image frames of a body lumen;
    a processing unit configured:
        to calculate a percentage of content in a subset of the plurality of image frames which was identified to include content,
        to calculate a cleanliness index of at least the subset of the plurality of image frames based on an average of said percentage of content derived from a subset of the plurality of image frames and
        to determine success of a preparatory procedure for cleaning the body lumen based on the cleanliness index; and
    a display to display the plurality of image frames and the cleanliness index of at least the subset of the plurality of image frames.

8. The system according to claim 7 comprising an external receiving device, wherein the processing unit is included in an external receiving device and wherein the external receiving device is to receive data wirelessly from the imaging device.

9. The system according to claim 7 wherein the processing unit is integral to a workstation.

10. The system according to claim 7 comprising a user input device for selecting a subset of the plurality of image frames.

11. The system according to claim 7 wherein the imaging device is an autonomous in-vivo device in the form of a capsule.

12. The system according to claim 7 wherein the display is included in a workstation.

* * * * *